United States Patent

Bedeschi et al.

[11] Patent Number: 5,840,899
[45] Date of Patent: *Nov. 24, 1998

[54] METHOD FOR THE PREPARATION OF 9-AMINO CAMPTOTHECIN

[75] Inventors: Angelo Bedeschi, Milan; Walter Cabri, Rozzano; Ilaria Candiani, Busto Arsizio; Franco Zarini, Settimo Milanese, all of Italy

[73] Assignee: Pharmacia S.p.A., Milan, Italy

[ * ] Notice: The term of this patent shall not extend beyond the expiration date of Pat. No. 5,614,628.

[21] Appl. No.: 602,792

[22] PCT Filed: May 4, 1995

[86] PCT No.: PCT/EP95/01692

§ 371 Date: Sep. 30, 1996

§ 102(e) Date: Sep. 30, 1996

[87] PCT Pub. No.: WO95/32207

PCT Pub. Date: Nov. 30, 1995

[30] Foreign Application Priority Data

May 24, 1994 [GB] United Kingdom .................. 9410388

[51] Int. Cl.⁶ ................................................. C07D 491/22
[52] U.S. Cl. ............................................................. 546/48
[58] Field of Search ................................ 546/48; 514/283

[56] References Cited

U.S. PATENT DOCUMENTS

| 5,106,742 | 4/1992 | Wall et al. ................. | 514/283 |
| 5,225,404 | 7/1993 | Giovanella et al. ............. | 514/283 |
| 5,602,141 | 2/1997 | Bedeschi ....................... | 514/283 |
| 5,614,628 | 3/1997 | Cabri et al. ................... | 546/48 |

FOREIGN PATENT DOCUMENTS 95-04736 1/1995 WIPO .

*Primary Examiner*—Donald G. Daus
*Attorney, Agent, or Firm*—Oblon, Spivak, McClelland, Maier & Neustadt, P.C.

[57] ABSTRACT

9-Amino camptothecin of formula (I)

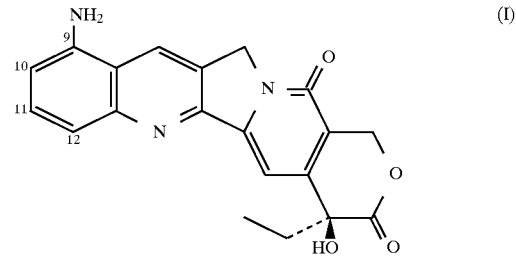

is prepared by:

1) reducing a compound of formula (II):

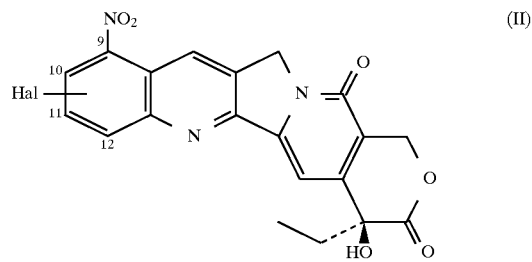

wherein Hal is 10- or 12-halogen, in a single step to the 9-amino-camptothecin of formula (I) or, alternatively, 2a) reductively removing the Hal group from a compound of formula (II) so obtaining the compound of formula (III):

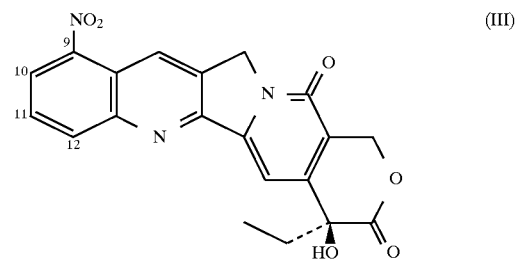

and
2b) reducing the compound of formula (III) so obtaining the 9-amino camptothecin of formula (I); the said steps 1 and 2a) and, optionally, step 2b) each being carried out in the presence of a catalytic amount of a compound of formula $PdL_2$ wherein L is acetate or halogen and, additionally, in the presence of an ammonium formate as a hydrogen source. The 9-amino camptothecin of formula (I) is useful as inhibitor of the enzyme topoisomerase I. It is useful in the treatment of cancers, in particular leukaemia, colon and rectal tumours.

14 Claims, No Drawings

METHOD FOR THE PREPARATION OF 9-AMINO CAMPTOTHECIN

FIELD OF THE INVENTION

The present invention relates to a new process for the preparation of 9-amino-20(S)-camptothecin of formula (I)

BACKGROUND OF THE INVENTION

In our patent application filed on Aug. 6, 1993 in the United Kingdom as UK 93 16352.5, a method for the preparation of 9-amino camptothecin comprising the steps illustrated in the below Scheme A was disclosed.

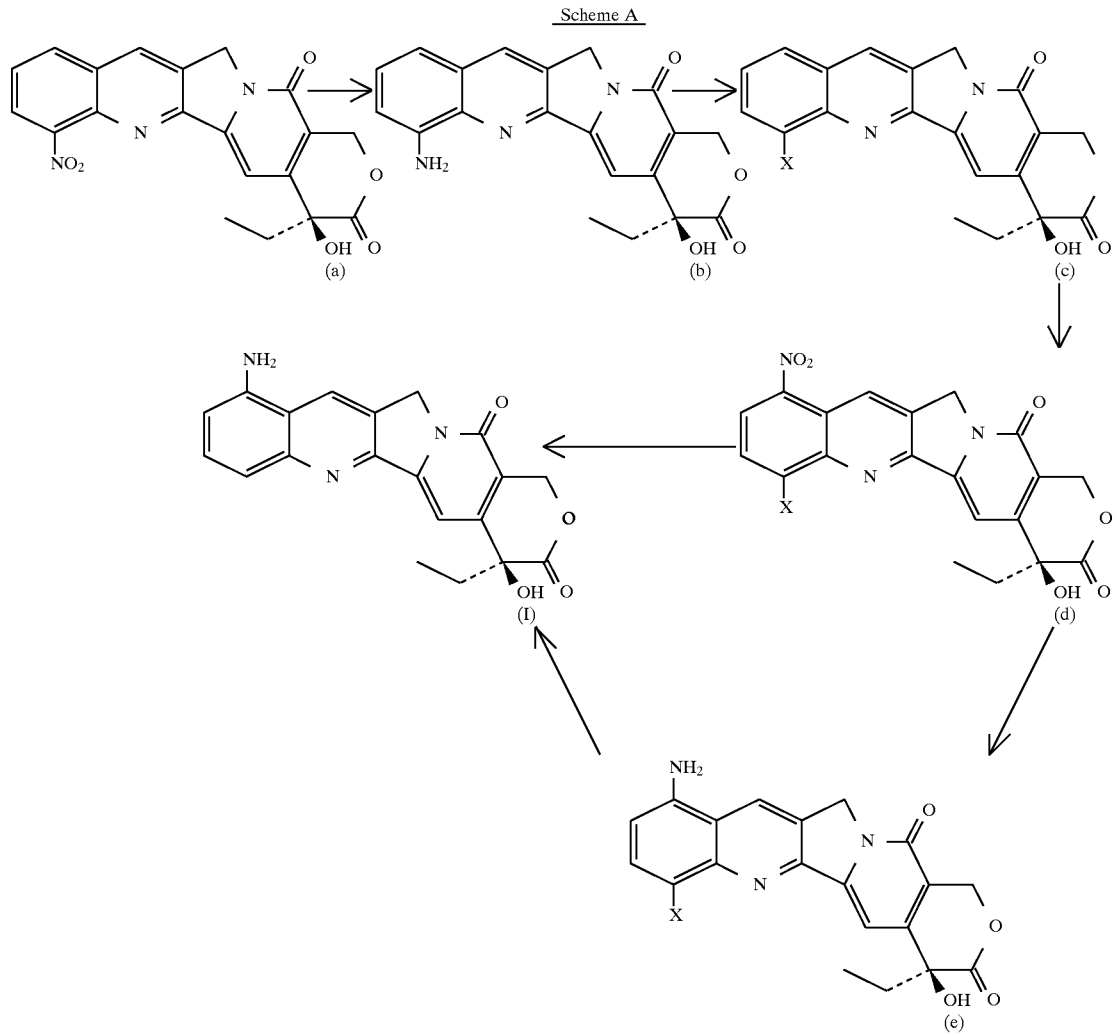

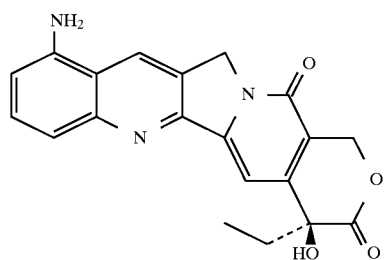

which is a known antitumor agent: Wani et al., J. Med. Chem. 1987, 30, 1774–1779; Hsiang et al., Cancer Res. 49, 4385–4389, Aug. 15, 1989; Cancer Res. 49, 1465–1469, Mar. 15, 1989.

wherein X is a group which can be removed reductively.

When the reduction of a compound of formula (d) wherein X is halogen is carried out in a single step by using, to catalyze this reaction, for example, palladium supported on Carbon (Pd/C), the desired product is obtained with an impurity of halo-amino derivative which is difficult to separate and consequently, it is a problem to isolate 9-amino camptothecin in pure form without affecting the overall yields.

We have found a new process which eliminates or minimises the presence of the undesired by-product and in the meantime permits the use not only of a 12-halogen, but also of a 10-halogen derivative as a substrate of the reductive reactions which lead to the 9-amino camptothecin.

Accordingly, the present invention provides a new process for preparing 9-amino camptothecin of formula (I) starting from a compound of formula (II), according to the steps illustrated in Scheme I below:

Scheme I

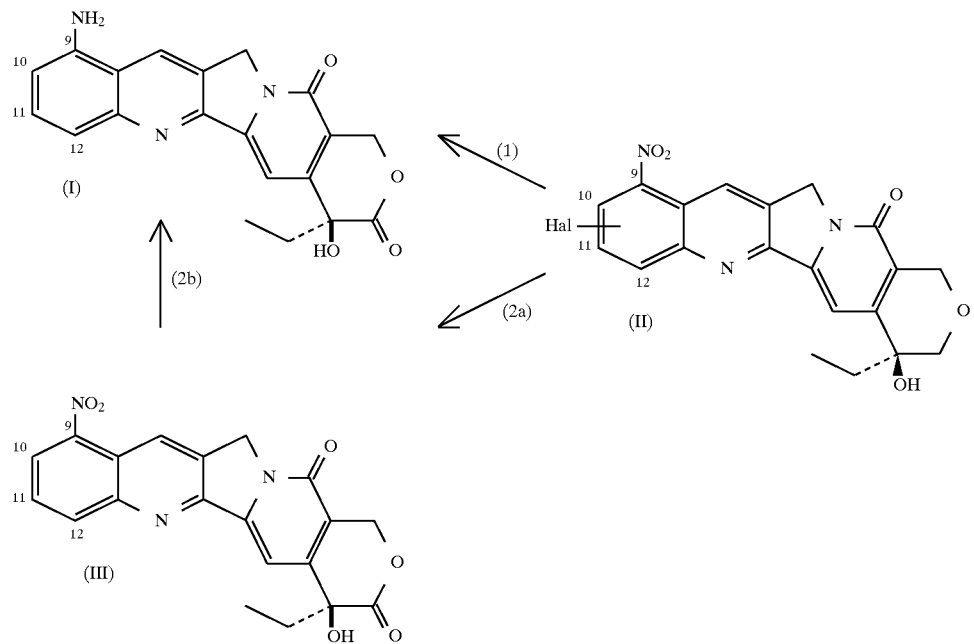

wherein Hal is 10- or 12-halogen.

The process comprises the reductive transformation of a 10- or 12-halogen derivative of formula (II) either in a single step, or alternatively, in two steps reducing first a compound of formula (II) to the compound of formula (III) and, further, reducing the compound of formula (III) to the compound of formula (I).

DETAILED DESCRIPTION OF THE INVENTION

The present invention provides a process for preparing 9-amino camptothecin of formula (I)

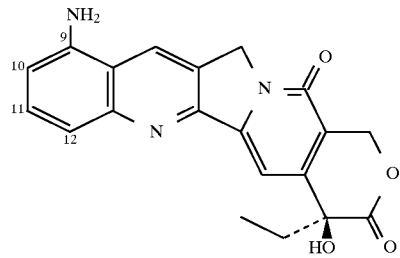

which comprises:

1) reducing a compound of formula (II)

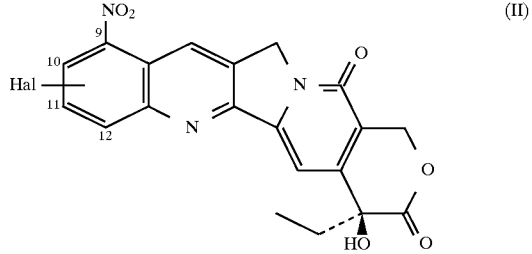

wherein Hal is 10- or 12-halogen, in a single step to the 9-amino camptothecin of formula (I) or, alternatively, 2a) reductively removing the Hal group from a compound of formula (II) so obtaining the compound of formula (III)

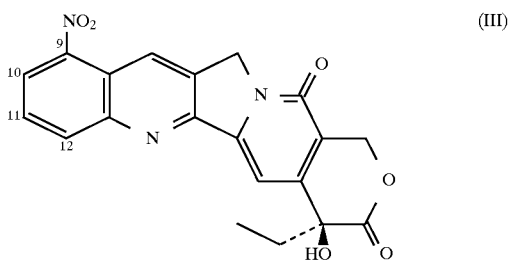

and 2b) reducing the compound of formula (III) so obtaining the 9-amino camptothecin of formula (I); the said steps. 1) and 2a) and, optionally, step 2b) each being carried out in the presence of a catalytic amount of a compound of formula $PdL_2$ wherein L is acetate (—COO—$CH_3$) or halogen and, additionally, in the presence of an ammonium formate as a hydrogen source.

In the formulae of the present specification, a dotted line ( ... ) indicates a substituent below the plane of the ring; a wedged line (z,1) indicates a substituent above the plane of the ring.

Preferably the halogen Hal is Br or Cl.

Preferably PdL$_2$ is Pd(OOC—CH$_3$)$_2$ or PdCl$_2$.

The reductions under steps 1), 2a) and, optionally, 2b) may each be carried out in the presence of a catalytic amount, for example from 0.01% to 0.2% by weight of a compound of formula PdL$_2$ wherein L is acetate or halogen and, additionally, in the presence of, for example, from 1 to 10 molar equivalents of a suitable ammonium formate such as ammonium formate or triethylammonium formate (which may be also prepared in situ). The reductions may be performed in a suitable solvent such as dimethylformamide (DMF), MeOH, CHCl$_3$, dioxane or mixture thereof. They are typically carried out at a temperature of from room temperature to about 150° C., preferably from about 40° C. to about 100° C. The reductions can each be carried out for a time which may vary from, for example, few minutes to one day, preferably from about 5 minutes to about 12 hours.

The reduction in step 1) may be carried out in the presence of, e.g., from 4 to 6 molar equivalents of an ammonium formate. Suitable ammonium formates are, for example, ammonium formate and triethylammonium formate. Step 1) can be effected for a time which may vary, e.g., from few hours to one day, preferably from about 3 hours to about 12 hours. The 9-amino camptothecin of formula (I) can thus be directly obtained as described under step 1).

When the alternative process is used, the reduction in step 2a) may be carried out in the presence of, e.g., from 1 to 3 molar equivalents of an ammonium formate. Suitable ammonium formates are, for example, ammonium formate and triethylammonium formate. Step 2a) can be effected for a time which may vary, e.g., from few minutes to few hours, preferably from about 5 minutes to about 5 hours. The compound of formula (III) may thus be obtained as described under step 2a).

The reduction of the 9-nitro derivative of formula (III), as described under step 2b), may be performed in a known manner, for example, with suitable reducing agents, or by catalytic reduction with suitable catalysts, in the presence of suitable reducing agents. For example, it may be performed as described in: J. March, Advanced Organic Chemistry, Third Edition, 1103.

For instance, the reduction may be performed with reducing agents such as SnCl$_2$ or other metals or metal salts, such as Zn or Fe and their salts. It can be carried out in a suitable solvent such as dilute aqueous HCl, a dilute aqueous protic acid, water, ethanol, methanol, or mixtures thereof. The temperature may be from about −20° C. to about 60° C. The reaction time may be from a few minutes to several days such as from 5 minutes to 3 days, for example from 4 hours to 24 hours.

The reduction of the compound of formula (III) to the compound of formula (I) may be alternatively carried out by the use of catalytic amounts of metals which perform nitro group reduction, such as palladium, platinum oxide, platinum, rhodium or ruthenium, in the presence of molecular hydrogen or hydrogen sources, such as triethylammonium formate, formic acid, tributyltin hydride, cyclohexadiene, etc. Such a reduction can be performed in a suitable solvent, such as DMF, MeOH, acetic acid, CHCl$_3$, dioxane or mixtures thereof. The temperature may be from about 0° C. to about 100° C. The reaction time may be from about 1 hour to about 3 days. The reduction may be performed at a pressure of from about 1 atm to about 100 atm.

Preferred reducing agents for the reduction from the compound of formula (III) to the compound of formula (I) are SnCl$_2$, in aqueous dilute HCl, at a temperature of from about 0° C. to about 60° C. for a period of from about 1 hour to about 2 days; or, by means of catalytic reduction, 5 or 10% Pd/C in DMF and PtO$_2$ and molecular hydrogen, at a temperature of from room temperature to about 60° C. for a time of from a few minutes, such as 5 minutes, to about 24 hours, and with a hydrogen pressure of from about 1 atm to abut 10 atm.

The reduction of the compound of formula (III) to the compound of formula (I) may also be performed in the presence of, e.g., from 3 to 6 preferably from 3 to 5, molar equivalents of an ammonium formate. Suitable ammonium formates are, for example, ammonium formate and triethylammonium formate. The reaction temperature can vary from about 20° C. to about 120° C., preferably from about 40° C. to about 100° C. The reaction time may vary from, e.g., few minutes to one day, preferably from about 1 hour to about 8 hours.

The reaction conditions characterizing the process of the present invention allow the (S) configuration at the 20-C position of the compound of formula (II) to be saved in the final 9-amino camptothecin of formula (I).

The starting compound of formula (II) is a known compound and may be prepared by known methods. For example it may be prepared by reacting a corresponding 10- or 12-halogen camptothecin derivative with a nitrating agent, such as nitric acid, mixtures of nitric and sulphuric acid, or other nitrating agents, such as potassium nitrate or nitric acid and boron trifluoride such as boron trifluoride monohydrate (see for instance Olah, G.A., et al. Synthesis 1085, 1992) or nitric acid/trifluoromethanesulfonic anhydride (ibid., 1087, 1992), at a temperature of from −20° to 100° C., for a time of from a few minutes to several days such as from 5 minutes to 3 days, for example from 4 hours to 24 hours.

The 10- or 12-halogen camptothecin derivatives may be obtained by known procedures see for example, Chem. Pharm. Bull., 39(12) 3183–3188, 1991.

The 9-amino camptothecin of formula (I) is useful as inhibitor of the enzyme topoisomerase I. It is useful in the treatment of cancers, in particular leukaemia, colon and rectal tumours. The compound may therefore be used to improve the condition of a patient suffering from such a cancer.

An effective amount of the 9-amino camptothecin may thus be administered to a host in need thereof, typically a human. The active compound can be administered by any appropriate route, for example orally, parenterally or intravenously. A dose of, e.g., from 0.1 to 60 mg of active compound can be given to a human patient per kg body weight by these routes. A preferred dosage range is from 1 to 40 mg per kg body weight.

The 9-amino camptothecin of formula (I) may be formulated for administration purposes into a pharmaceutical composition with a pharmaceutically acceptable carrier or diluent. Any suitable carrier or diluent may be employed, depending upon the route of administration. Suitable types of formulations are described in U.S. Pat. No. 5,106,742 and WO 91/05556.

The following Examples illustrate the preparation of the intermediates and end compounds of the process of the present invention and do not limit the scope of the invention.

EXAMPLE 1

9-amino camptothecin.

12-bromo-9-nitro camptothecin (0.5 g) was dissolved in distilled DMF (25 ml). Palladium acetate (0.06 g) formic acid (0.193 ml) and triethylamine (0.71 ml) were added. The solution was heated to 80° C., and the heating was continued for 12 hours. Charcoal was added and the mixture was filtered hot through a celite filter aid. The filtrate was concentrated in vacuo, and the precipitated orange solid was collected by filtration to yield 0.3 g of 9-amino camptothecin.

EXAMPLE 2

9-nitro camptothecin 12-bromo-9-nitro camptothecin (0.5 g) was dissolved in distilled DMF (25 ml). Palladium acetate (0.06 g), formic acid (0.058 ml), and triethylamine (0.212 ml) were added. The solution was heated to 80° C., and the heating was continued for 2.5 hours. The mixture was cooled and filtered through a celite filter aid. The filtrate was concentrated in vacuo, and the residue was purified by chromatography eluting with $CH_2Cl_2$/EtOAc mixtures. There were obtained 0.35 g of 9-nitro camptothecin.

EXAMPLE 3

9-amino camptothecin 9-nitro camptothecin (3.4 g) was dissolved in distilled DMF (100 ml). Palladium acetate (0.08 g), formic acid (0.95 ml), and triethylamine (3.5 ml) were added. The solution was heated to 80° C., and the heating was continued for 1 hour. DMF (200 ml) and charcoal were added to the reaction mixture, and the stirring was continued for 0.5 hours at 80° C. The mixture was filtered hot through a celite filter aid, and the filtrate was concentrated to small volume. The precipitated orange solid was collected by filtration to yield 2.5 g of 9-amino camptothecin.

EXAMPLE 4

9-nitro camptothecin 12-bromo-9-nitro camptothecin (0.1 g) was dissolved in distiled DMF (3 ml). Palladium chloride (0.01 g), formic acid (0.013 ml), and triethylamine (0.048 ml) were added. The solution was heated to 80° C., and the heating was continued for 2 hours. The mixture was cooled and filtered through a celite filter aid. The filtrate was concentrated in vacuo, and the residue was purified by chromatography eluting with $CH_2Cl_2$/EtOAc mixtures. There were obtained 0.065 g of 9-nitro camptothecin.

EXAMPLE 5

9-nitro camptothecin 12-chloro-9-nitro camptothecin (0.06 g) was dissolved in distilled DMF (3 ml). Palladium acetate (0.004 g), formic acid (0.008 ml), and triethylamine (0.028 ml) were added. The solution was heated to 80° C., and the heating was continued for 2 hours. The mixture was cooled and filtered through a celite filter aid. The filtrate was concentrated in vacuo, and the residue was purified by chromatography eluting with $CH_2Cl_2$/EtOAc mixtures. There were obtained 0.035 g of 9-nitro camptothecin.

EXAMPLE 6

9-nitro camptothecin 12-chloro-9-nitro camptothecin (0.06 g) was dissolved in distilled DMF (3 ml). Palladium chloride (0.004 g), formic acid (0.008 ml), and triethylamine (0.028 ml) were added. The solution was heated to 80° C., and the heating was continued for 1 hour. The mixture was cooled and filtered through a celite filter aid. The filtrate was concentrated in vacuo, and the residue was purified by chromatography eluting with $CH_2Cl_2$/EtOAc mixtures. There were obtained 0.038 g of 9-nitro camptothecin.

EXAMPLE 7

9-amino camptothecin

The reaction was performed as described in Example 1, except that 10-bromo-9-nitro camptothecin (0.5 g) was used as starting material. 0.25 g of the title product were obtained.

EXAMPLE 8

9-nitro camptothecin

The reaction was performed as described in Example 2, except that 10-bromo-9-nitro camptothecin (0.5 g) was used as starting material. 0.3 g of the title product were obtained.

EXAMPLE 9

9-amino camptothecin

The reaction was performed as described in example 1, except that 12-chloro-9-nitro camptothecin (0.5 g) was used as starting material. 0.2 g of the title product were obtained.

We claim:

1. A process for preparing 9-amino camptothecin of formula (I):

which comprises:

1) reducing a compound of formula (II):

wherein Hal is 10- or 12-halogen, in a single step to the 9-amino-camptothecin of formula (I) or, alternatively, 2a) reductively removing the Hal group from a compound of formula (II) so obtaining the compound of formula (III):

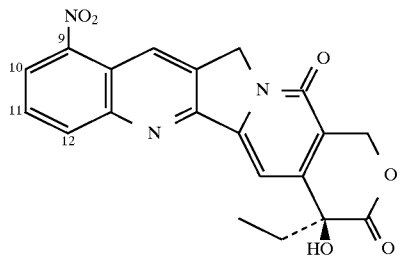

and 2b) reducing the compound of formula (III) so obtaining the 9-amino camptothecin of formula (I); the said steps 1 and 2a) and, optionally, step 2b) each being carried out in the presence of a catalytic amount of a compound of formula $PdL_2$ wherein L is acetate or halogen and, additionally, in the presence of an ammonium formate as a hydrogen source.

2. A process according to claim 1 wherein steps 1) and 2a) and, optionally, step 2b) are each carried out in the presence of from 0.0% to 0.2% by weight of the compound of formula $PdL_2$ and, additionally, in the presence of from 1 to 10 molar equivalents of the ammonium formate.

3. A process according to claim 1 wherein steps 1), 2a) and, optionally, 2b) are each carried out at a temperature of from about 40° C. to about 100° C.

4. A process according to claim 1 wherein steps 1), 2a) and, optionally, 2b) are each carried out for a time of from about 5 minutes to about 12 hours.

5. A process according to claim 1 wherein step 1) is carried out in the presence of from 4 to 6 molar equivalents of an ammonium formate.

6. A process according to claim 1 wherein step 1) is carried out for a time of from about 3 hours to about 12 hours.

7. A process according to claim 1 wherein step 2a) is carried out in the presence of from 1 to 3 molar equivalents of an ammonium formate.

8. A process according to claim 1 wherein step 2a) is carried out for a time of from about 5 minutes to 5 hours.

9. A process according to claim 1 wherein step 2b) is carried out in the presence of from 3 to 6 molar equivalents of an ammonium formate.

10. A process according to claim 1 wherein step 2b) is carried out for a time of from about 1 hour to about 8 hours.

11. A process according to claim 1 wherein the compound of formula $PdL_2$ is $Pd(OOC-CH_3)_2$.

12. A process according to claim 1 wherein the compound of formula $PdL_2$ is $PdCl_2$.

13. A process according to claim 1 wherein steps 1), 2a) and, optionally, 2b) are each carried out in the presence of ammonium formate.

14. A process according to claim 1 wherein steps 1), 2a) and, optionally, 2b) are each carried out in the presence of triethylammonium formate.

* * * * *